United States Patent [19]
Main et al.

[11] Patent Number: 5,104,025
[45] Date of Patent: Apr. 14, 1992

[54] INTRALUMINAL ANASTOMOTIC SURGICAL STAPLER WITH DETACHED ANVIL

[75] Inventors: Lauren O. Main, Loveland; Federico Bilotti, Madeira, both of Ohio

[73] Assignee: Ethicon, Inc., Somerville, N.J.

[21] Appl. No.: 590,404

[22] Filed: Sep. 28, 1990

[51] Int. Cl.[5] .......................................... A61B 17/115
[52] U.S. Cl. .................................... 227/175; 227/19; 227/179
[58] Field of Search ................. 227/175, 179, 180, 19

[56] References Cited

U.S. PATENT DOCUMENTS

| | | | |
|---|---|---|---|
| 3,388,847 | 6/1968 | Kasulin et al. | 227/19 |
| 4,319,576 | 3/1982 | Rothfuss | 128/305 |
| 4,603,693 | 8/1986 | Conta et al. | 128/305 |
| 4,817,847 | 4/1989 | Redtenbacher et al. | 227/19 |

FOREIGN PATENT DOCUMENTS

| | | |
|---|---|---|
| 0293123A2 | 5/1988 | European Pat. Off. |
| 7711347 | 10/1977 | Netherlands. |

Primary Examiner—Mark Rosenbaum
Assistant Examiner—Rinaldi Rada
Attorney, Agent, or Firm—Paul A. Coletti

[57] ABSTRACT

A surgical stapling mechanism with an integral trocar is disclosed. This trocar contains an alignment mechanism which causes the anvils on the stapler to align with the staples held within the head portion. A unique latching mechanism is disclosed, and a sleeve which covers the sharp trocar tip is provided.

40 Claims, 6 Drawing Sheets

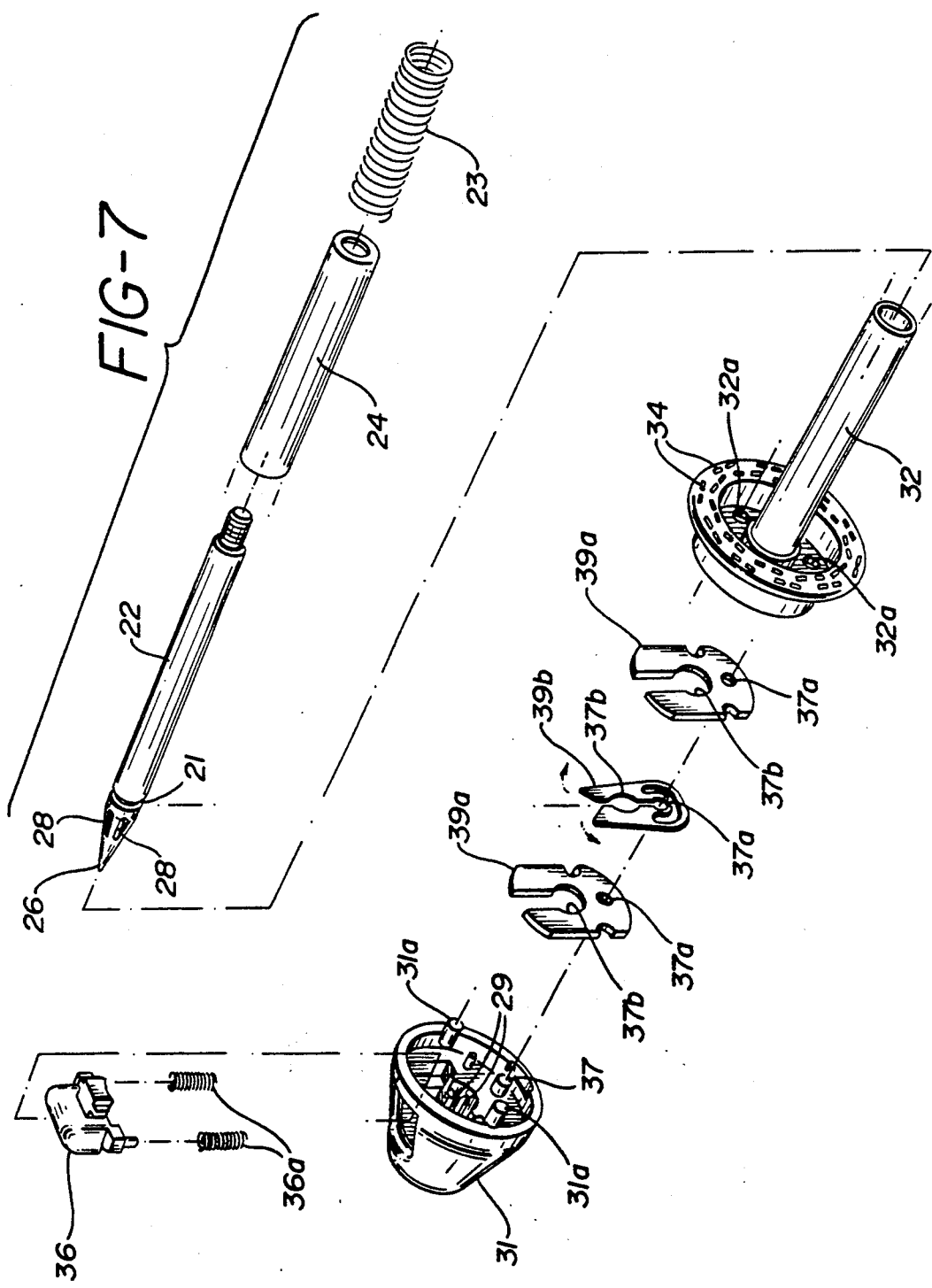

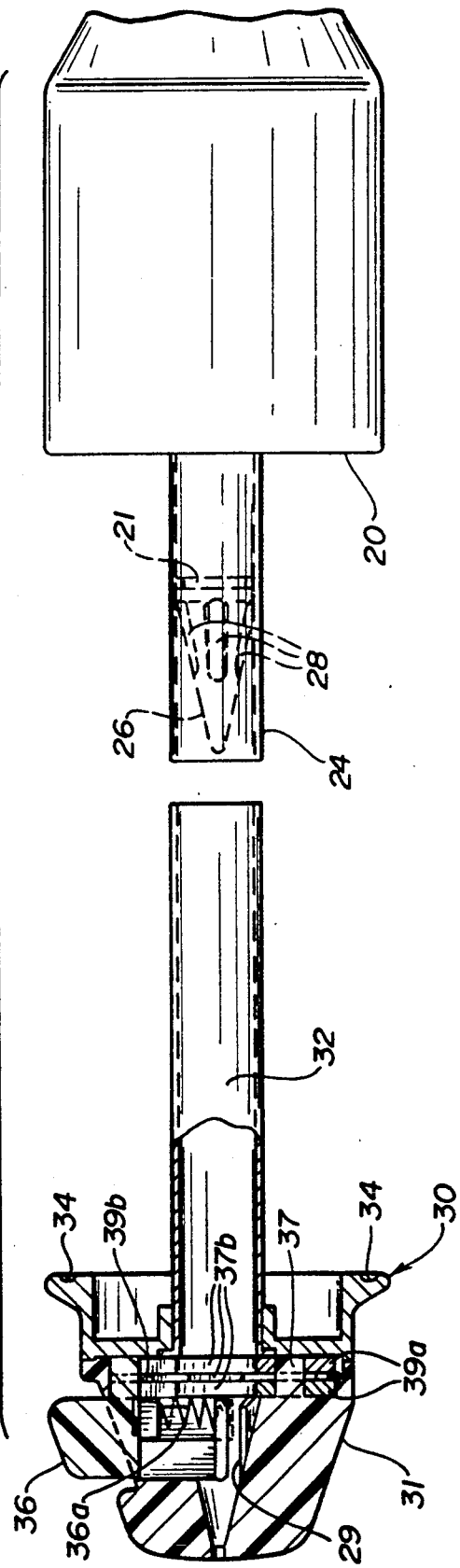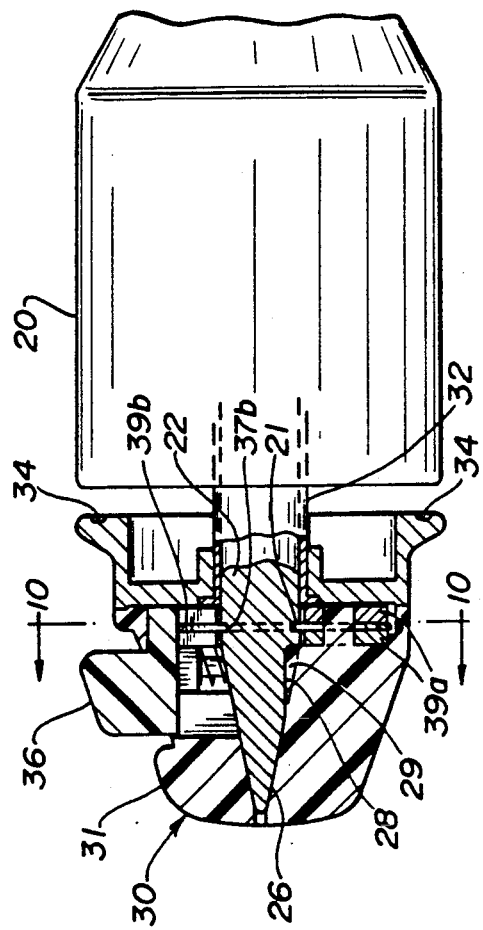

INTRALUMINAL ANASTOMOTIC SURGICAL STAPLER WITH DETACHED ANVIL

FIELD OF THE INVENTION

This invention relates to surgical stapling. More specifically, this invention relates to internal anastomotic stapling. Most specifically, this invention relates to internal anastomotic stapling of lumen, particularly the intestines, wherein a circular ring of staples is applied to the desired lumen.

BACKGROUND OF THE INVENTION

Generally, surgical stapling has made substantial advances in the past decades. Specifically, in the area of internal anastomotic stapling the advances have been quite dramatic. Devices such as the Proximate TM ILS stapler, produced by the assignee of the present invention, Ethicon, Inc., Somerville, N.J., have enabled surgeons to perform operations and procedures which were heretofore perceived as difficult, if not impossible, with relative ease.

In performing surgical anastomotic stapling, generally the two pieces of lumen are attached by a ring of staples. During this procedure, a circular knife blade is used to separate tissue which is held within the circular ring. The circular ring is then removed with the stapler so that a circular opening withing the lumen is completed along the surgical stapling line.

In performing these surgical procedures however, it has become desirable to separate the anvil head on which the staples are clinched from the stapling portion from which the staples are expelled. Advances along these lines have been made in the past. It has been typical in the past that the stapling side of the mechanism is attached the head to the anvil portion through a "purse-stringed" gathering of tissue.

In addition, it has been found that when the tissue contained on the head portion of the stapler is attached to tissue contained on the anvil portion of the stapler, it is difficult to connect the anvil and head with proper alignment of the staples into the anvils contained on the anvil side.

Further, it has been found that it is difficult to perform such stapling within a circular stapler such that the head size is kept to a minimum on the outside with a maximum inner cavity, so that more tissue can be gathered within the anastomosed staple.

Also, although it may be desirable as part of this invention to have the tissue which is gathered, pierced by a relatively sharp trocar tip on the stapler head, it is not always desirable for the stapler head to be continually exposed with a sharp trocar tip. Rather, it has been found that it is more desirable feature is to have a sharp tip exposed only during a portion of the attachment procedure.

SUMMARY OF THE INVENTION

Accordingly, it is an object of the invention to provide a surgical stapler for anastomotic stapling in which there is a separable anvil portion connectable to a stapling portion and a trocar integral to the instrument on the stapling portion of the instrument.

It is a further object of this invention to provide the anvil portion with an extended tube in order to facilitate purse stringing of tissue.

Moreover it is another object of the invention to provide an alignment mechanism aligning the anvil portion and the staples on the head or stapling portion of the shaft.

It is further an object of the invention to provide a means of engaging the anvil portion of the shaft through the tip of the integral trocar.

It is yet another object of the invention to provide a means wherein the trocar tip is shielded except for a connection to the anvil portion of the shaft or during purse-stringing.

These and other objects of the invention are described in a surgical stapling device where staples are driven from the head portion into the anvil portion of the device. The anvil portion is detachable from the head portion, and the head portion contains a trocar tip upon which is attached the anvil. The anvil portion contains an elongated sleeve which contains an opening through which is placed the trocar tip. On the trocar tip there are means which are engagable with a latching mechanism on the anvil portion. There are contained alignment means which align the anvil portion with staples on the head portion of the instrument. There may also be contained on the trocar tip a spring-loaded sleeve which is retractable to expose the tip upon insertion through purse-stringed tissue, or insertion of the anvil shaft onto the trocar tip.

The objects of this invention are more apparent when taking into account the following drawings in conjunction with the Detailed Description of the Invention.

DESCRIPTION OF THE DRAWINGS

FIG. 7 is exploded perspective view of an anvil, anvil shaft and trocar of the present invention;

FIG. 8 is a side view in partial cross-section of the anvil taken along lines 8—8 of FIG. 2;

FIG. 9 is a side view in partial cross-section of a closed anvil shaft seated upon a trocar tip as described in the present invention;

DETAILED DESCRIPTION OF THE INVENTION

Figure 1:
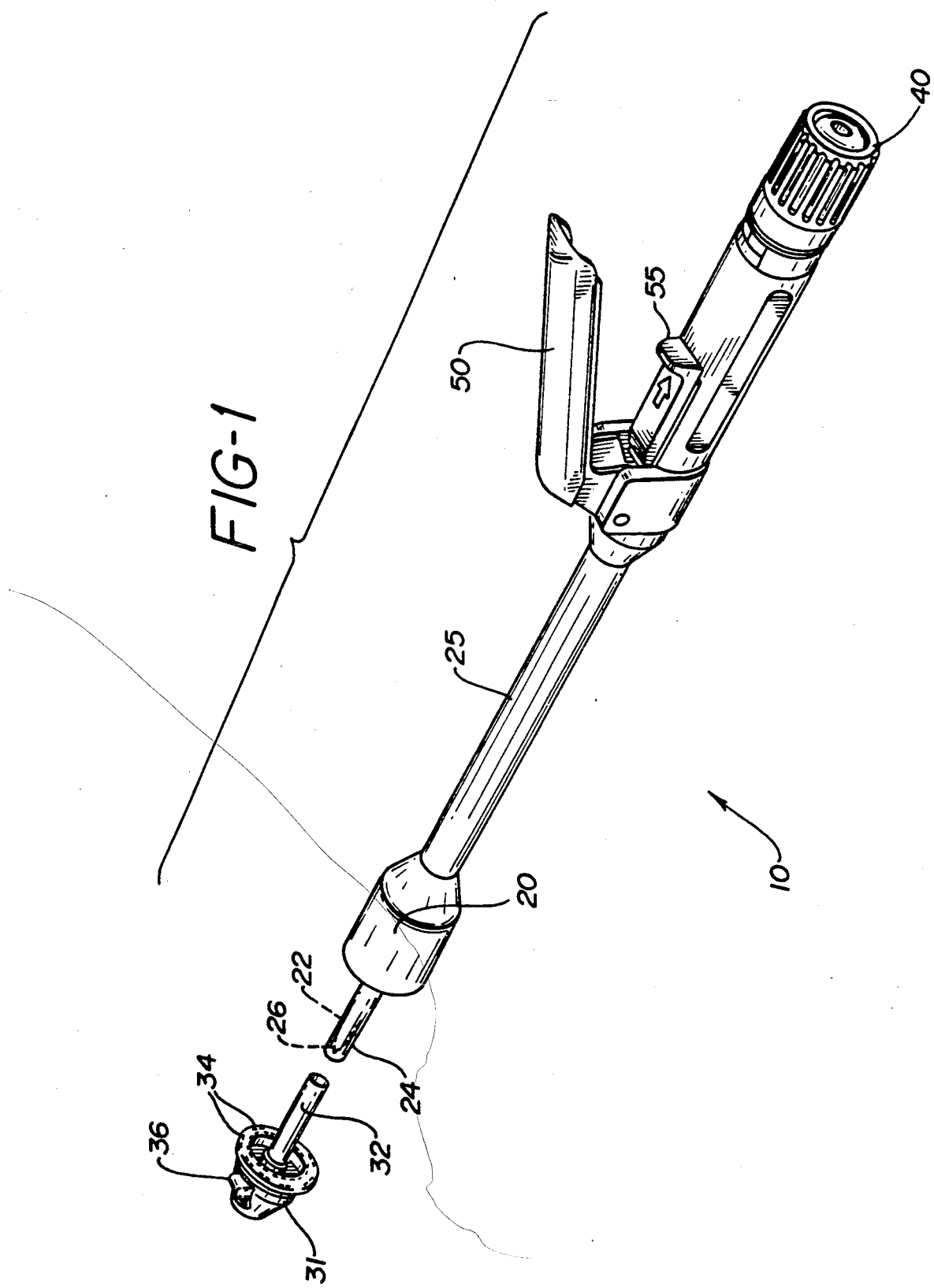
FIG. 1 is a perspective view of a surgical stapler of the present invention.

As seen in FIG. 1, there is disclosed a stapler 10 containing head 20, an anvil 30, an adjusting screw 40, and trigger 50. The trigger 50 acts to operate the stapler 10 when safety 55 is released. When trigger 50 is activated, a firing mechanism not shown operates within shaft 25 so that staples are expelled from the head 20. These staples are clinched about anvils 34 displayed circumferentially about the head 31 of the anvil 30. Simultaneously, a knife held within the head 20 acts to cut tissue held within the circumference of the stapled tissue between anvils 34. In this way, a circular lumen may be pulled through the shaft and leave a closed tissue about the stapler 10. The stapler 10 is then pulled through the tissue leaving stapled tissue in its place.

Figure 2:
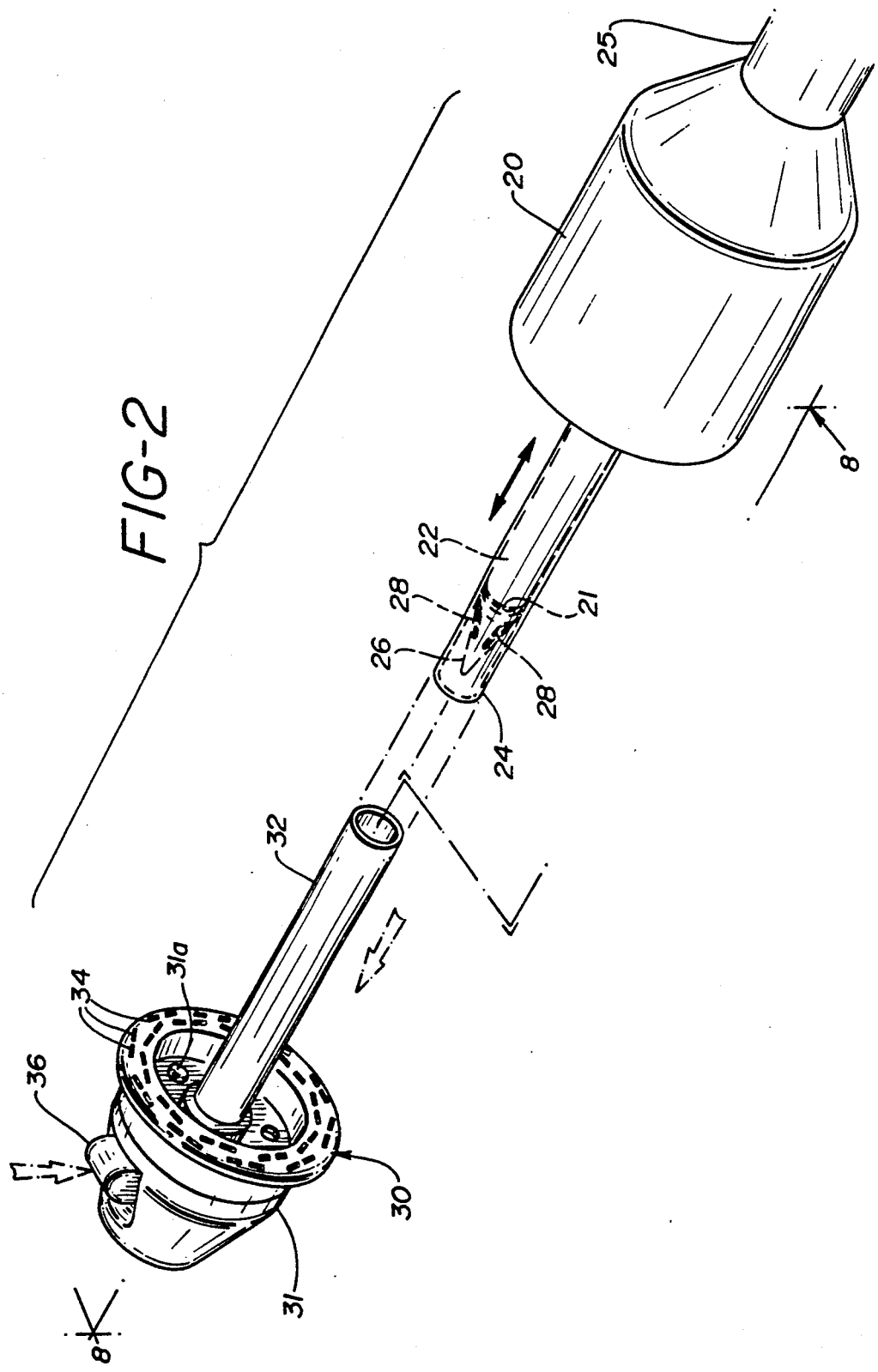
FIG. 2 is a perspective view of the head and anvil portion of a surgical stapler of the present invention.

As seen in FIGS. 1, 2 and 7 there are various mechanisms which form the invention in this circular anastomotic stapler. More specifically, as seen in FIGS. 1 and 2, there is disclosed a trocar shaft 22 containing trocar tip 26. This trocar shaft 22 is contained integral to the head portion 20 and is capable of piercing tissue. This trocar shaft 22 is surrounded by sleeve 24 which reciprocates into and out of the head 20. The sleeve 24 is held onto the head 20 by spring 23 which creates its resiliency and allows reciprocation of sleeve 24 about trocar shaft 22.

Figure 3:
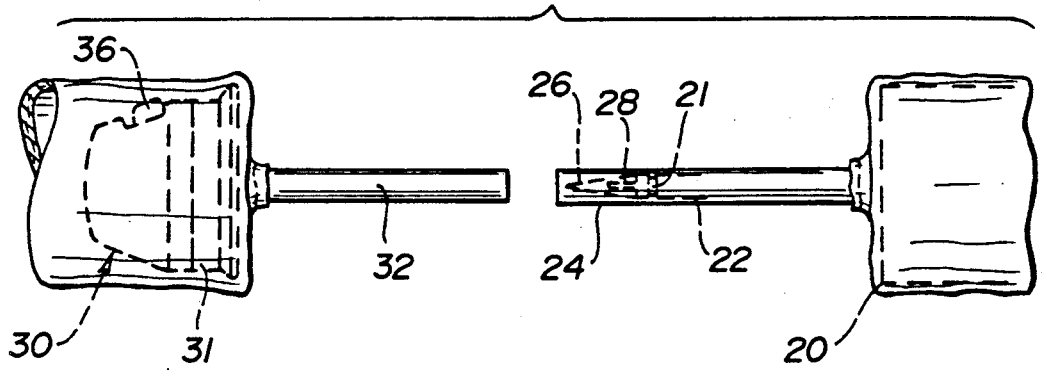
FIGS. 3, 4, 5 and 6 are side views of a closing and stapling operation of the present invention.
Figure 11:
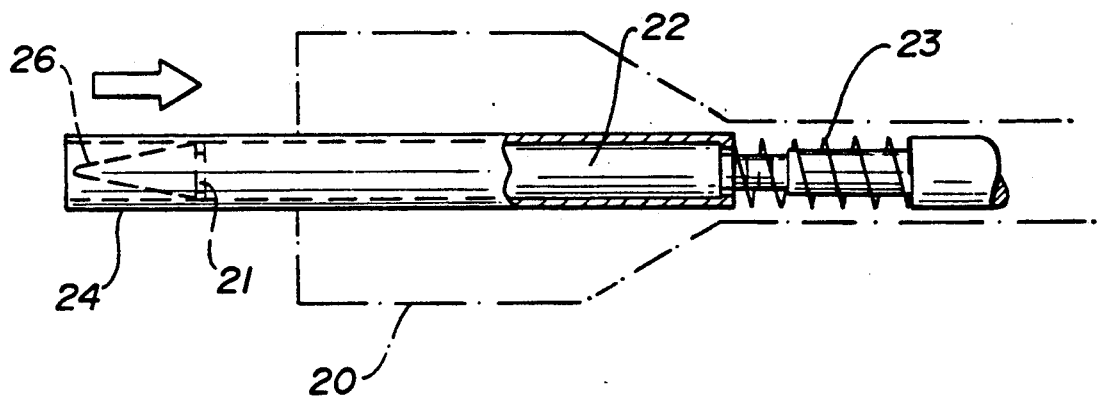
FIG. 11 is a partial cut away side view of a trocar sheathing mechanism contained in the head portion of the present invention.

As seen in FIGS. 3 and 11, the trocar shaft 22 would generally be covered by sleeve 24 so that purse-stringed tissue may be placed over the sleeve 24. Nonetheless, the trocar tip 26 is capable of puncturing through tissue when pressure is applied. This is especially useful when connecting purse stringed tissue. In this way, the trocar sleeve 24 with tip 26 exposed is capable of being forced through a purse string so that the purse string is not broken. After the trocar sleeve is forced through the tissue, the sleeve 24 surrounds the trocar tip 26 so that no further damage will be done and yet, the lumen is adequately attached over the sleeve 24.

Corresponding to the trocar portion 24, there is the anvil portion 30. On the anvil 30, there are contained anvils 34 displayed circumferentially around anvil head 31. These anvils 34 correspond to staples held circumferentially within head 20. As will be noticed in FIG. 3, the anvil 30 may be placed within a lumen of tissue, and then the tissue purse stringed about shaft 32. Contained within anvil 30 there is an alignment mechanism which is further disclosed in FIG. 8. As seen in FIG. 8 there are serrations 29 contained within the anvil head 31. These serrations correspond with indentations or recesses 28 contained on the tip of the trocar 26. When anvil 30 is placed over trocar shaft 22, the serrations 29 find corresponding recesses 28 and therefore are able to align anvils 34 with the staples placed circumferentially about the head 20.

Figure 10:
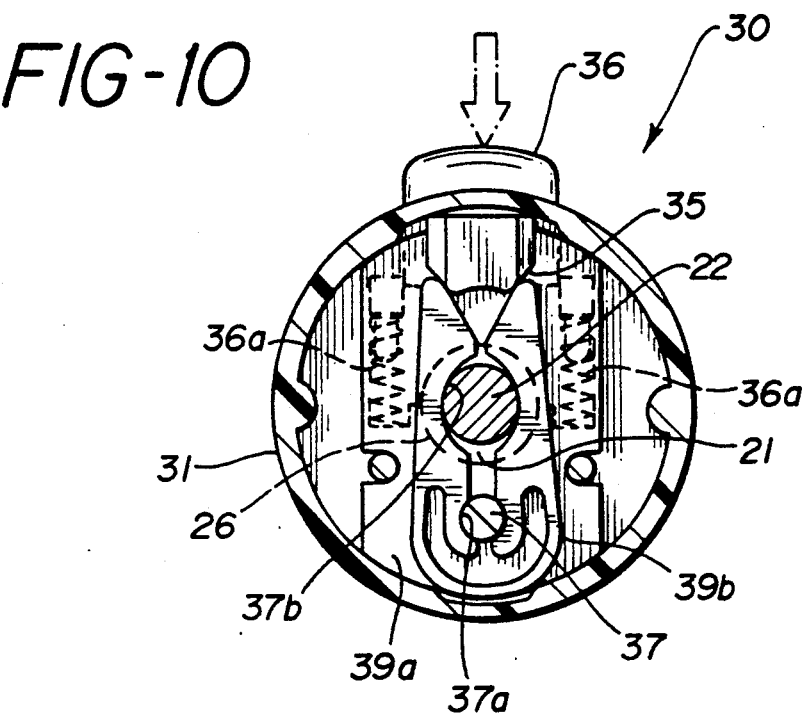
FIG. 10 is a cross-sectional top view of an anvil shaft taken along lines 10—10 of FIG. 9.

Furthermore, there is disclosed a unique method of latching and unlatching the anvil to the head. More specifically, as seen in FIGS. 2 and 7, release 36 is formed from a button-shaped lever which is contained by release spring 36a on the head 31 of the anvil 30. This release contains a wedge 35, as seen in FIG. 10 which forces open the central alignment locking clip 39b. This locking clip is wedged between alignment clips 39a. Each of these clips 39a, 39b has a centrally bored trocar hole 37b and holes 37a which fit on pin 37 in the head 31.

The trocar tip 26 of trocar 22 is able to fit through the centrally displayed holes 37b. When it is desired to lock the anvil 30 upon the head 20, the generally springed locking clip 39b is forced open and then closes shut around indentation or ridge 21 on trocar tip 22. This is best seen in FIGS. 8 and 10. When it is desired to open the anvil 30 and separate it from the trocar shaft, force is placed on release 36 such that wedge 35 pries open the prongs of locking clip 39b. Hole 37b in clip 39b is now the same size as holes 37b in each of the alignment clips 39a. In this way the shaft is slidable out of the anvil shaft 32.

However, normally the spring which forms the locking clip 39b is biased in such a fashion that it is generally in a smaller or "closed" position, such that it would fit within indentation or ridge 21. Indentation 21 holds the locking clip 39b, and the anvil 30 is adequately secured on the trocar 22 contained within head 20.

Figure 4:
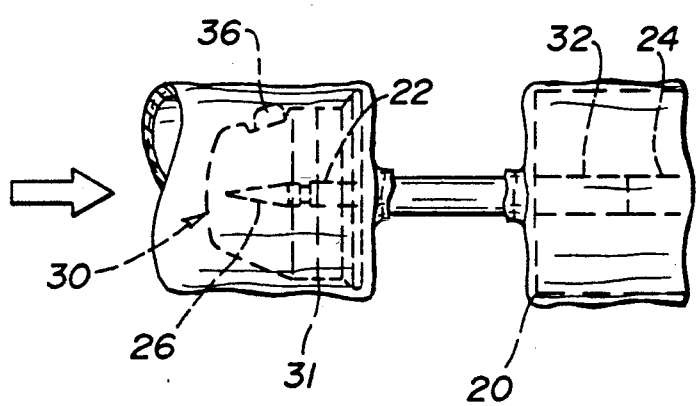
Figure 5:
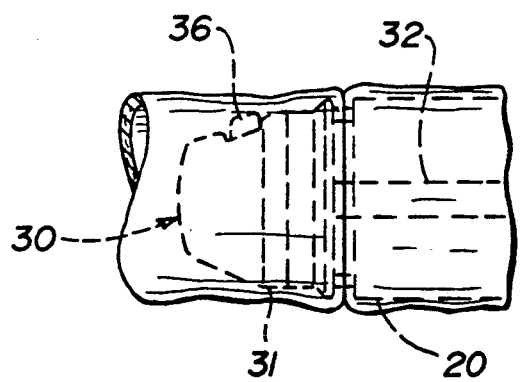

In operation therefore as seen in FIGS. 3, 4, 5 and 6, the anvil with two lumen attached to both the shaft 22 and tubular anvil extension 32 respectively, is ready for surgery. As seen in FIG. 4, the anvil 30 is placed onto shaft 22 such that trocar tip 26 is exposed and fits within anvil extension 32. The sleeve 24 is pushed to an exposed position so that it is telescoped within the head 20. The holes 37b in alignment clips 39a and locking clip 39b guide the trocar through extension 32 into anvil head 31. When the trocar is adequately seated within anvil head 31, locking clip 39b which contains the wedge shape spring is caused to open and then grip about the indentation 21. Because the recesses 28 have aligned themselves with serrations 29 in the shaft 31, it is ensured that the anvils 34 are aligned with the staples contained in the head 20. As better seen in FIG. 7, serrations 29 have been aligned with anvils 34 during manufacture through accurate placement of bosses 31a into holes 32a when connecting anvil head 31 to extension 32. The instrument now appears as two proximated pieces of lumen as in FIG. 5. The adjusting screw 40 has pulled the tissue closer to each other.

Figure 6:
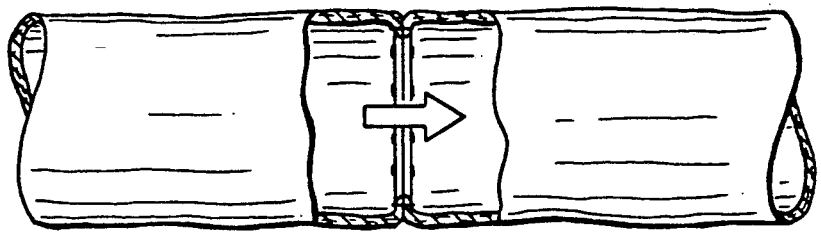

As seen in FIG. 6, the staples have been fired into the anvils through the tissue. Once the staples are clinched, a knife which cuts tissue held within the circumference of the staples. Once this cutting is effected, the stapler 10 is pulled in the direction of the head 20 and through the lumen so that a circumferentially closed lumen with a inner tubular opening is now created.

After removing the stapler 10, the excess lumen held in stapler 10 is disposed. The release 36 on anvil 30 is pressed, as seen in FIG. 2 and 10. This causes the locked mechanism as seen in FIG. 9 to open as alluded to in FIG. 7. The locking clip 39b now opens, allowing the user to slide the anvil shaft 32 from the stapler head 20. In this way the tissue that is held within the anvil 30 and head 20 is removed.

In this way there has been proper purse-stringing and puncture by trocar 22, alignment between recesses 28 and serrations 29, pull through of anvil head 31, locking clip 39b about the indention 21, and proper stapling and cutting of the tissue. It is therefore to be realized that the following claims and their equivalents are meant to encompass the scope of the invention.

What is claimed is:

1. A surgical stapling device comprising:
   a plurality of staples, said staples initially contained in a head portion;
   an anvil portion into which said staples may be ejected from said head portion, said anvil portion detachable from said head portion;
   said head portion containing a shaft with a longitudinal axis and having an integral trocar with a sharpened generally conical tip, said sharpened tip having aligning means displayed radially about said tip extending and parallel to said shaft longitudinal axis for aligning said tip with said anvil portion; and
   wherein said anvil portion further contains an anvil head having a plurality of staple clinching anvils and attached to an elongated sleeve with a hollow interior and said anvil head further containing a plurality of ribs placed radially within said sleeve hollow exterior, said ribs aligning with said trocar tip aligning means.

2. The device of claim 1 wherein said aligning means comprises a plurality of grooves engageable with said ribs such that said staples are aligned with said anvils on said anvil portion when said ribs are inserted into said grooves.

3. The device of claim 2 wherein said anvil portion contains a latching mechanism which is engageable with said trocar tip.

4. The device of claim 3 wherein said latching mechanism further contains a release mechanism which enables said anvil portion to be released from said trocar tip.

5. The device of claim 4 wherein said latching mechanism is a spring loaded clip engageable about said trocar.

6. The device of claim 5 wherein said release mechanism contains a manually operated wedge operable to release said spring loaded clip from about said trocar.

7. The device of claim 3 wherein said trocar tip contains engagement means engageable with said latching mechanism.

8. The device of claim 3 wherein said trocar shaft contains an indented ridge around which is engageable said latching means.

9. The device of claim 2 wherein said trocar tip is protected by a spring loaded sleeve, said sleeve retractable to expose said tip upon the insertion of said anvil portion elongated sleeve over said trocar.

10. The device of claim 2 wherein said trocar tip is retractable into the head portion of said device with said anvil connected to said trocar.

11. The device of claim 2 wherein said tip is retractable into said head through operation of a retracting means connected to said tip along the shaft of said head portion.

12. The device of claim 11 wherein said retracting means comprise a screw mechanism operable to retract said trocar tip into said head portion.

13. A surgical stapling device comprising:
   a plurality of staples, said staples initially contained in a head portion;
   an anvil portion into which said stapled may be ejected from said head portion, said anvil portion detachable from said head portion; and
   said head portion containing a shaft having a longitudinal axis and with an integral trocar having a sharpened generally conical tip, and aid trocar tip containing a plurality of grooves parallel with said shaft longitudinal axis.

14. The device of claim 13, wherein said anvil portion contains an elongated sleeve, said sleeve containing an opening through which is placed said trocar tip.

15. The device of claim 14 wherein said trocar tip is protected by a spring loaded sleeve, said sleeve retractable to expose said tip upon the insertion of said anvil portion elongated sleeve over said trocar.

16. The device of claim 14 wherein said anvil portion contains an anvil head connected to said elongated sleeve, said anvil head having a plurality of ribs displayed radially about an inner diameter, and said plurality of trocar tip grooves align with said ribs upon insertion of said tip into said elongated sleeve and said head.

17. The device of claim 13 wherein said anvil portion contains a latching mechanism for latching said anvil portion to said trocar tip.

18. The device of claim 17 wherein said latching mechanism further contains a release mechanism which enables said anvil portion to be released from said trocar tip.

19. The device of claim 17 wherein said trocar tip contains engagement means for engaging said latching mechanism.

20. The device of claim 17 wherein said latching mechanism is a spring loaded clip engageable about said trocar.

21. The device of claim 17 wherein said trocar contains a shaft having an indented ridge around which is engageable said latching means.

22. A surgical stapling device comprising:
   a plurality of staples, said staples initially contained in a head portion;
   an anvil portion into which said staples may be ejected from said head portion, said anvil portion detachable from said head portion;
   said head portion containing a shaft with a trocar having a sharpened tip upon which may be attached said anvil portion, and said head portion further containing a first elongated sleeve, said first elongated sleeve attached to said trocar by spring means; and
   wherein said trocar tip may be exposed upon the exertion of force on said sleeve, and wherein said anvil portion is attachable to said exposed trocar tip.

23. The device of claim 22 further containing retracting means connected to said trocar tip, said trocar tip retractable into said head portion with said anvil attached thereon by use of said retracting means.

24. The device of claim 23 wherein said anvil portion contains a second elongated sleeve, said second sleeve containing an opening through which is placed said trocar tip.

25. The device of claim 23 wherein said anvil portion contains a latching mechanism which is engageable with said trocar tip.

26. The device of claim 25 wherein said latching mechanism further contains a release mechanism which enables said anvil portion to be released from said trocar tip.

27. The device of claim 25 wherein said trocar tip contains engagement means for engaging said latching mechanism.

28. The device of claim 25 wherein said latching mechanism is a spring loaded clip engageable about said trocar.

29. The device of claim 25 wherein said trocar contains a shaft having an indented ridge around which is engageable said latching means.

30. The device of claim 25 wherein said anvil portion contains an anvil head connected to said elongated sleeve, said anvil head having a plurality of ribs displayed radially about an inner diameter, and said trocar contains a plurality of grooves displayed radially about said tip, said grooves aligning with said ribs upon insertion of said tip into said elongated sleeve and said head.

31. A surgical stapling device comprising:
   a plurality of staples, said staples initially contained in a head portion;
   an anvil portion into which said staples may be ejected from said head portion, said anvil portion detachable from said head portion;
   said head portion further containing a shaft having a longitudinal axis, and an integral trocar having a sharpened tip, and further containing retracting means, said trocar tip retractable into a retracted position on said shaft along said longitudinal axis by operation of said retracting means; and
   wherein said anvil portion contains a latching mechanism engageable with said trocar tip and operable to keep said anvil releasably engaged to said head portion, and further wherein said anvil portion is not releasable from said head portion when said anvil portion is attached to said head portion with said trocar tip in its retracted position.

32. The device of claim 31 wherein said anvil portion contains an elongated sleeve, said sleeve containing an opening through which is placed said trocar tip.

33. The device of claim 31 wherein said latching mechanism further contains a release mechanism which enables said anvil portion to be released from said trocar tip.

34. The device of claim 31 wherein said trocar tip contains engagement means for engaging said latching mechanism.

35. The device of claim 31 wherein said latching mechanism is a spring loaded clip engageable about said trocar.

36. The device of claim 35 wherein said release mechanism contains a manually operated wedge operable to release the grip of said spring loaded clip from about said trocar tip.

37. The device of claim 31 wherein said trocar contains a shaft having an indented ridge around which is engageable said latching means.

38. The device of claim 31 wherein said trocar tip is protected by a spring loaded sleeve, said sleeve retractable to expose said tip upon the insertion of said anvil portion elongated sleeve over said trocar.

39. The device of claim 31 wherein said anvil portion contains an anvil head connected to said elongated sleeve, said anvil head having a plurality of ribs displayed radially about an inner diameter, and said trocar contains a plurality of grooves displayed radially about said tip, said grooves aligning with said ribs upon insertion of said tip into said elongated sleeve and said head.

40. The device of claim 31 wherein said retracting means comprise a screw mechanism operable to retract said trocar tip into said head portion.

* * * * *